US00PP17388P3

(12) United States Plant Patent

Izhar

(10) Patent No.: US PP17,388 P3

(45) Date of Patent: Jan. 30, 2007

(54) STRAWBERRY PLANT NAMED 'YUVAL'

(50) Latin Name: *Fragaria×ananassa*
Varietal Denomination: Yuval

(75) Inventor: Shamay Izhar, Rehovot (IL)

(73) Assignee: Fertiseeds Ltd., Nez Ziona (IL)

( * ) Notice: Subject to any disclaimer, the term of this patent is extended or adjusted under 35 U.S.C. 154(b) by 0 days.

(21) Appl. No.: 10/688,683

(22) Filed: Oct. 17, 2003

(65) Prior Publication Data

US 2004/0133953 P1 Jul. 8, 2004

(30) Foreign Application Priority Data

Oct. 21, 2002 (IL) ..... PBR 03428

(51) Int. Cl.
*A01H 5/00* (2006.01)

(52) U.S. Cl. ..... Plt./209

(58) Field of Classification Search ..... Plt./209
See application file for complete search history.

*Primary Examiner*—Kent Bell
*Assistant Examiner*—June Hwu
(74) *Attorney, Agent, or Firm*—Stratton Ballew PLLC

(57) ABSTRACT

A new and distinct cultivar of *Fragaria×ananassa* is disclosed. 'Yuval' grows from September and produces fruit starting in November and lasting until the following summer. The production of the fruit beginning in November (Northern Hemisphere, latitude 30–33 degrees) is two months earlier than short day varieties of *Fragaria* species. The fruit of 'Yuval' is characterized by a unique, uniform color, as well as a very desirable taste, texture, shape and size.

2 Drawing Sheets

Latin name of the genus and species of the plant claimed: *Fragaria×ananassa.*
Variety denomination: 'Yuval'.

CROSS-REFERENCE TO RELATED APPLICATIONS

This application claims priority of Israel Plant Breeder's rights application Ser. No 3428/02, filed Oct. 21, 2002.

BACKGROUND OF THE INVENTION

This new variety was developed from an organized, scientifically designated, breeding program, carried out by Fertiseeds LTD, Rehovot, Israel. This new variety originated as a single seedling selected from a seedling population obtained by a cross in March 2000 between female line #7 (a single plant selection from a selfing population of variety 'Tamar,' U.S. Plant Pat No. 11,135) and breeding line #3 (a single plant selection from a selfing population of variety 'Bella,' unpatented). A single plant selection from the cross between Line #7 and Line #3 was propagated by runners and subsequently reproduced by meristem culture at Sharon Valley, Israel in August 2000. In every generation (three generations) the plant populations were observed carefully for variants and off types—no variants or off types were found.

BRIEF SUMMARY OF THE INVENTION

'Yuval' is a new and distinct cultivar of *Fragaria× ananassa.* Yuval is able to grow from September and produce fruits starting in November and lasting until the following summer. The production of the fruit beginning in November (Northern Hemisphere, latitude 30–33 degrees) is two months earlier than short day varieties of *Fragaria* species. The fruit of the "Yuval" variety is characterized by a unique, uniform color, as well as very desireable tast, texture, shape and size.

BRIEF DESCRIPTION OF THE PHOTOGRAPH

DETAILED BOTANICAL DESCRIPTION

Figure 1:
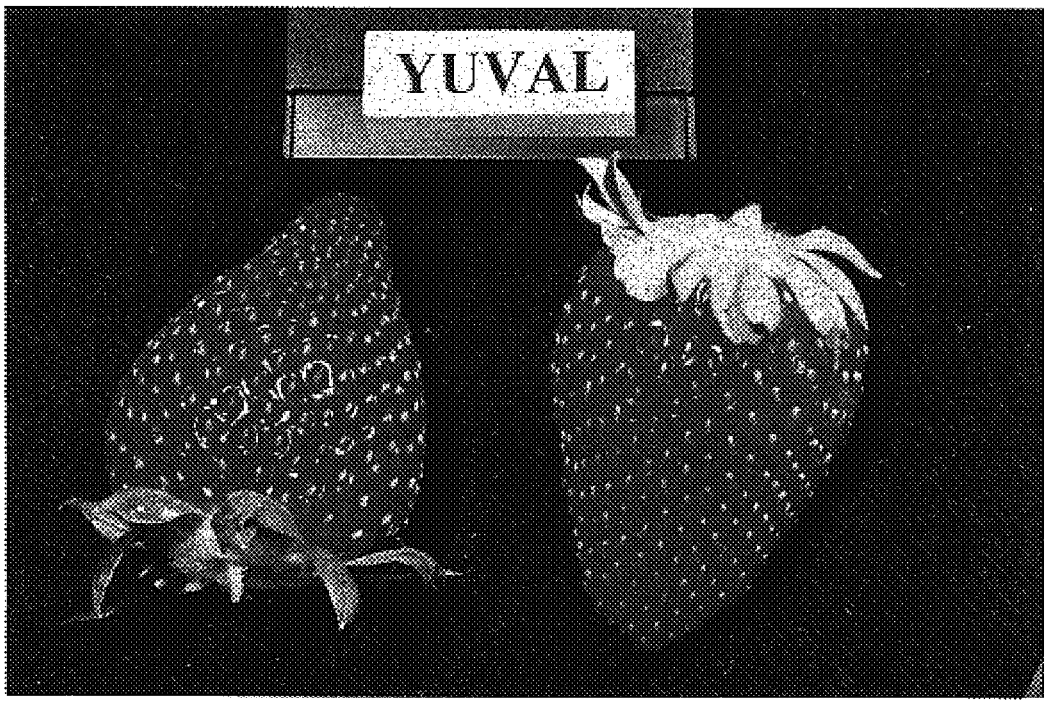
FIG. 1 is a photograph of the "Yuval" variety, illustrating the fruit.
Figure 2:
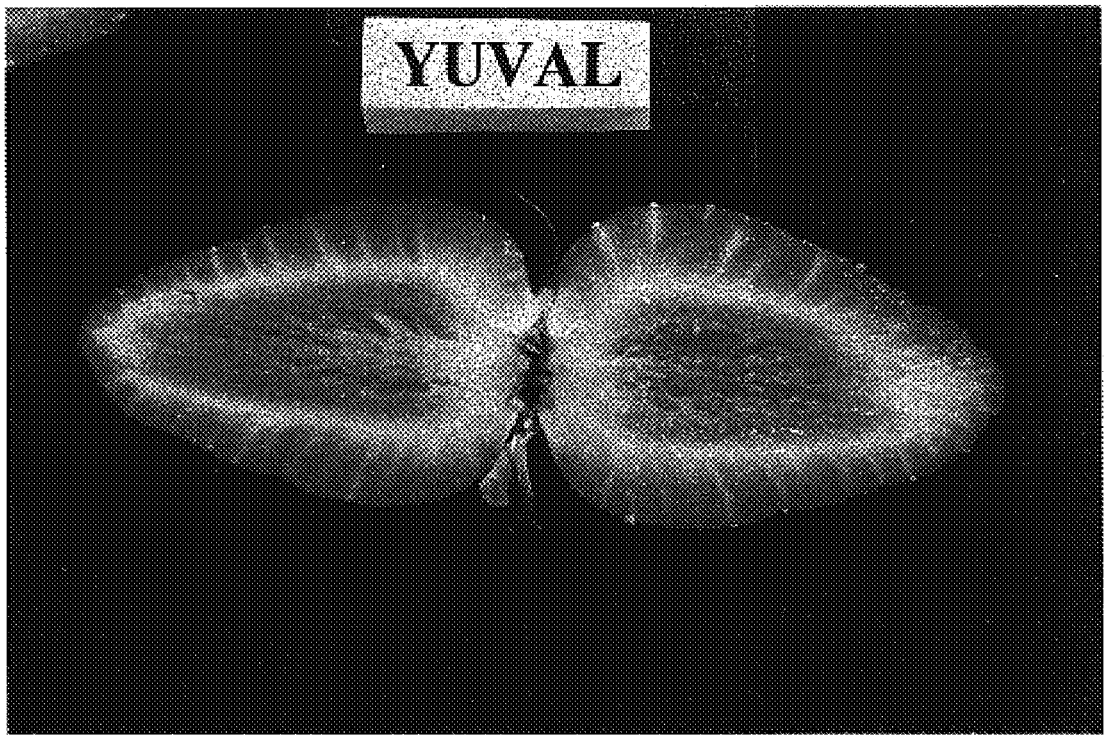
FIG. 2 is a photograph of the "Yuval" variety, illustrating a cross section of the fruit.

The "Yuval" variety was grown in fall-winter, under polyethylene tunnels in Israel. "Yuval" is an 'infra short day' variety, flowering earlier than 'short day' type strawberry varieties. Infra-Short-Day (I.S.D) varieties are defined as varieties which initiate floral bud primordia under regimes of 13–14 hours at the time that night temperatures are about 22° C. to 26° C., compared to strawberry types classified as 'short day', that do not initiate floral bud primordia under above mentioned conditions, thus resulting in early flowering and fruit production. Flowering and fruit production are affected by the use of polyethylene tunnels, protecting the plants against wind, and more importantly against rain, which causes malformation of the fruit as well as fruit decay.

This production technique, when practiced by the skilled artisan, does not involve temperature or light control, but normal field conditions. Mother plants were stored at 2° C. from December/January through April. They were planted in the nursery without further treatment. Runners with plantlets were produced during summer. These young plantlets were collected from the nursery in September and transferred to raised beds. Average temperatures at that time of the year are 30° C. during the day and 22° C. at night. Water and fertilizers were applied through drip irrigation.

An example of an optimum planting date is between September 15 and 25, with the approximate date of flowering from October 5 to 15 and the approximate date of first fruiting from November 5 to 25. Flowering is not induced by chilling, but by natural exposure to short days (13–14 hours) characteristic of late summer.

'Yuval' has no tendency toward fruit malformation. Disease tolerance in 'Yuval' appears normal in that no particular problematic conditions arose during trials. However, there were indications that 'Yuval' is tolerant to Phytophthera. The type of bearing is remontant, i.e., 'Yuval' blooms continuously during late fall, winter and spring.

The fruit shape of 'Yuval' is similar to the strawberry variety 'Dorit' (U.S. Plant Pat. No. 7,869). The fruit is longer than broad, with primary, secondary and tertiary fruit possessing almost similar shape. The fruit is of good firmness with a red color.

'Yuval' flowers two months earlier than known short day strawberry varieties. A close known variety would be 'Dorit' (U.S. Plant Pat. No. 7,869); also see the new varieties 'Sharon' (U.S. Plant Pat. No. 7,881); 'Shalom' (U.S. Plant Pat. No. 7,876); 'Smadar' (U.S. Plant Pat. No. 7,865); 'Ofra' (U.S. Plant Pat. No. 8,746); 'Virginia' (U.S. Plant Pat. No. 8,748; 'Nama' (U.S. Plant Pat. No. 8,747). Additionally, early flowering results in early fruit production.

A comparison of 'Yuval' to 'Bella' and 'Tamar' reveals a number of distinguishing characteristics, as illustrated in Table 1:

TABLE 1

| Characteristic | 'Yuval' | 'Bella' | 'Tamar' |
|---|---|---|---|
| Date flowering begins* | Very early | Early | Very early to early |
| Fruit color | Red | Light red | Red |
| Fruit shape | Ovate perfect | Ovate to round | Ovate to conical |
| Uniformity of fruit | Very uniform | Not uniform | Not uniform |
| Fruit malformation | Very uniform | Light malformation | Malformed |
| Plant vigor | Compact | Compact | Vigorous |
| Fruit size | Medium small | Medium | Large to medium |

*Under prevailing conditions in Sharon Valley, Israel

The following is a detailed botanical description of 'Yuval,' based on observations made at Rehovot, Israel. Color readings described herein were taken under natural light conditions and color identifications were made by reference to The Royal Horticultural Society Colour Chart, except where common terms of color definition are employed. It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Plant:
1. *Height.*—14–19 cm.
2. *Diameter.*—25–30 cm.
3. *Habit.*—Compact.
4. *Density.*—Dense.
5. *Vigor.*—Medium.

Leaf:
1. *Length.*—18–22 cm.
2. *Width.*—12–16 cm.
3. *Green color of upper side.*—Medium RHS 147A, 147B (Compare to 'Dorit').
4. *Blistering.*—Medium.
5. *Cross section.*—Concave.
6. *No. of leaflets.*—Usually 2 to 3.

Petiole:
1. *Length.*—10–12 cm.
2. *Thickness.*—3–4 mm.
3. *Pubescence.*—Medium.
4. *Green color.*—Light green RHS 144B.

Terminal leaflet:
1. *Length/width ratio.*—Longer than broad.
2. *Shape of base.*—Obtuse.
3. *Shape of teeth.*—Rounded.
4. *Length.*—5–8 cm.
5. *Width.*—5–7 cm.

Calyx:
1. *Diameter of primary calyx.*—20–40 mm.
2. *Diameter of secondary calyx.*—20–30 mm.
3. *Diameter of tertiary calyx.*—20–30 mm.
4. *Size of inner calyx in relation to outer calyx.*—Same size.
5. *Calyx color.*—Light green RHS 144B.

Flower:
1. *Diameter of primary flower.*—20–26 mm.
2. *Diameter of secondary flower.*—20–26 mm.
3. *Diameter of tertiary flower.*—20–26 mm.
4. *Spacing of petals.*—Overlapping.
5. *Petal length.*—10–12 mm.
6. *Petal width.*—10–14 mm.
7. *Petal length/width.*—Broader than long.
8. *Time of beginning of flowering.*—Very early (approximately the first week of October under the prevailing conditions); compare to 'Dorit'.
9. *Fragrance.*—Mild.

Stolon:
1. *Number per plant.*—Many.
2. *Thickness.*—3.5–4 mm.
3. *Pubescence.*—Weak.
4. *Anthocyanin coloration.*—Very weak.

Inflorescence:
1. *Position relative to foliage.*—Same.
2. *Peduncle length.*—Ca. 11 cm.
3. *Peduncle thickness.*—Ca. 3 mm.
4. *Peduncle color.*—Light green RHS 144B.
5. *Peduncle pubescence.*—Medium dense.

Fruit:
*Time of first ripening.*—Very Early (first week of November in Hod HaSharon, Israel).

Primary fruit:
1. *Length.*—40–50 mm.
2. *Width.*—35–50 mm.
3. *Shape.*—Cordial; similar to 'Dorit,' but without the tendency to produce malformed fruits.
4. *Weight.*—Ca. 25 g.

Secondary fruit:
1. *Length.*—36–50 mm.
2. *Width.*—30–40 mm.
3. *Shape.*—Cordial.
4. *Weight.*—Ca. 24 g.

Tertiary fruit:
1. *Length.*—30–45 mm.
2. *Width.*—25–35 mm.
3. *Shape.*—Cordial.
4. *Weight.*—Ca. 24 g.

Fruit:
1. *Band without achenes.*—Narrow.
2. *Unevenness of surface.*—Very weak.
3. *Color.*—Red 44 A.
4. *Evenness of color.*—Even.
5. *Glossiness.*—Very Strong.

*6. Insertions of achenes.*—Level with surface.
*7. Insertions of calyx.*—Below Surface.
*8. Rose of calyx segments.*—Detached.
*9. Size of calyx in relation to fruit diameter.*—Smaller.
*10. Adherence of calyx.*—Strong.
*11. Firmness.*—Medium-firm.
*12. Color of flesh.*—Orange-red 43A.
*13. Evenness of flesh color.*—Uneven.
*14. Sweetness.*—Strong.
*15. Acidity.*—Weak-medium.
*16. Yield.*—Very high (See Table 2).
*17. Eating quality.*—(Excellent (See Table 3).
*18. Fruit structure.*—Semi-hollow.
*19. Color of achenes.*—Light brown to deep yellow.

TABLE 2

COMPARATIVE YIELD OF 'YUVAL'

| | November | December | January | February | March | April |
|---|---|---|---|---|---|---|
| 'Yuval' | 60 | 80 | 100 | 80 | 120 | 160 |
| 'Dorit' | 30 | 70 | 100 | 100 | 100 | 100 |
| 'Ofra' | 50 | 60 | 60 | 100 | 100 | 100 |
| 'Chandler' | 0 | 0 | 30 | 150 | 150 | 120 |

Note: Average yield in g./plant in Hod HaSharon, Israel.

TABLE 3

COMPARATIVE FRUIT CHARACTERISTICS OF 'YUVAL'

| | T.S.S. | Acidity | Aroma | Taste |
|---|---|---|---|---|
| Yuval | 8.5–11.0 | 1.0 | 5 | Excellent |
| Dorit | 8.5–9.5 | 1.0 | 5 | Good |
| Ofra | 8.0–9.5 | 1.0 | 4 | Good |
| Chandler | 6.5–7.5 | 0.8 | 4 | Slightly acidic |

Notes:

1. T.S.S.—Total Soluble Solids (Sugars) expresses fruit sweetness and was determined with a refractometer.
2. Percent of acidity was determined as follows: 2 cc juice extract was mixed with 20 cc. water. Five drops of phenolphthalein was added and the mixture was titrated with NaOH. The percent acidity is calculated as the quantity of NaOH(cc)×0.32.

What is claimed is:

1. I claim a new and distinct strawberry plant substantially as shown and described herein.

* * * * *